United States Patent
Cooke et al.

(10) Patent No.: US 7,626,171 B2
(45) Date of Patent: Dec. 1, 2009

(54) METHOD OF CONSTRUCTING TIME-IN-FLIGHT PET IMAGES

(75) Inventors: Steven E. Cooke, Garfield Heights, OH (US); Donald R. Wellnitz, Fitchburg, WI (US); Thomas L. Laurence, North Royalton, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 35 days.

(21) Appl. No.: 12/159,795

(22) PCT Filed: Jan. 4, 2007

(86) PCT No.: PCT/US2007/060078

§ 371 (c)(1),
(2), (4) Date: Jul. 1, 2008

(87) PCT Pub. No.: WO2007/082126

PCT Pub. Date: Jul. 19, 2007

(65) Prior Publication Data

US 2008/0296505 A1    Dec. 4, 2008

Related U.S. Application Data

(60) Provisional application No. 60/757,281, filed on Jan. 9, 2006.

(51) Int. Cl.
*G01T 1/164* (2006.01)
*G01T 1/166* (2006.01)

(52) U.S. Cl. .............................. 250/363.03; 250/363.04

(58) Field of Classification Search ............ 250/363.03, 250/363.04
See application file for complete search history.

(56) References Cited

U.S. PATENT DOCUMENTS

| | | | |
|---|---|---|---|
| 4,395,635 A | 7/1983 | Friauf et al. | |
| 4,980,552 A | 12/1990 | Cho et al. | |
| 5,841,140 A | 11/1998 | McCroskey et al. | |
| 2001/0040219 A1 | 11/2001 | Cherry et al. | |
| 2003/0226972 A1 | 12/2003 | Wong et al. | |
| 2006/0102846 A1* | 5/2006 | Manjeshwar et al. | ... 250/363.03 |
| 2007/0040122 A1* | 2/2007 | Manjeshwar et al. | ... 250/363.03 |

* cited by examiner

*Primary Examiner*—David P Porta
*Assistant Examiner*—Mindy Vu

(57) ABSTRACT

A method of reconstructing time-of-flight (TOF) images includes obtaining a profile of a subject to be imaged in an examination region (14) of an imaging system (10), Events associated with radiation emitted from the subject are detected and converted to electronic data. Electronic data attributable to radiation events located outside the profile are removed and images are reconstructed from the remaining electronic data.

24 Claims, 4 Drawing Sheets

METHOD OF CONSTRUCTING TIME-IN-FLIGHT PET IMAGES

CROSS REFERENCE TO RELATED APPLICATIONS

This application claims the benefit of U.S. Provisional Application Ser. No. 60/757,281 filed Jan. 9, 2006, which is incorporated herein by reference.

The following relates to medical imaging systems. It finds particular application to radiation event processing. More particularly, it is directed towards discarding detected radiation events that are not within a pre-determined region of interest of a subject prior to reconstructing images in medical imaging systems such as a time-of-flight Positron Emission Tomography (TOF-PET) scanner.

A conventional PET system has a plurality of radiation detector modules arranged around an imaging region. The radiation detectors are configured to detect gamma rays produced within the imaging region. Such gamma rays include gamma rays resulting from electron-positron annihilation events, for instance, in which positrons emitted during radiation decay interact with electrons to produce pairs of oppositely directed gamma rays. Pairs of oppositely directed gamma rays are subsequently detected by two different radiation detectors as two substantially simultaneous radiation events that define a line of response (LOR) between the detectors. A time difference between the times of each event of each coincident pair is analyzed to localize the positron-electron annihilation event along a LOR. A windowing technique determines which of these events are conveyed to an image reconstruction system and which events are discarded. For example, events within the window are deemed likely to be relevant and are conveyed to the image reconstruction system; whereas, events outside of the window are deemed artifact and discarded.

With conventional TOP-PET systems, the window is defined based on a radius of a bore (which defines an imaging region) and is based on an intrinsic timing resolution of the imaging system. Conventionally, the window of TOF-PET systems is a constant size, regardless of the procedure and/or subject being scanned. TOF-PET scanners have sub-nanosecond resolution which allows events within the window to be localized along the LOR.

As a result, some of the detected events are not "true" coincidence events. Instead, they represent scattered radiation, randoms (e.g., two unrelated radiation events that are detected in sufficiently close temporal proximity and appear to be a coincident event), and the like. Such events lead to reduced image quality, for example, by reducing contrast resolution. Most reconstruction processes include post-reconstruction algorithms that remove these artifacts from the reconstructed image, for example, after the data has already been substantially processed. However, reconstructing bad data consumes processing cycles and decreases overall system performance, compounded by farther post-reconstruction artifact correction processing.

In view of the aforementioned deficiencies with conventional imaging systems, there is an unresolved need for processing techniques that improve system performance.

In one aspect, a method of reconstructing time-of-flight (TOF) images is illustrated. The method includes obtaining a profile of a subject to be imaged in an examination region of an imaging system. Events associated with radiation emitted from the subject are detected and converted to electronic data. Electronic data attributable to radiation events located outside the profile of the subject are removed and images are reconstructed from the remaining electronic data.

One advantage includes accelerated reconstruction attributable to filtering extraneous radiation events prior to reconstruction.

Another advantage resides in reconstructed images with reduced artifact contamination.

Another advantage is that artifact removal algorithms can be simplified.

Still further advantages will become apparent to those of ordinary skill in the art upon reading and understanding the detailed description of the preferred embodiments.

The drawings are only for purposes of illustrating embodiments and are not to be construed as limiting the claims.

Figure 1:
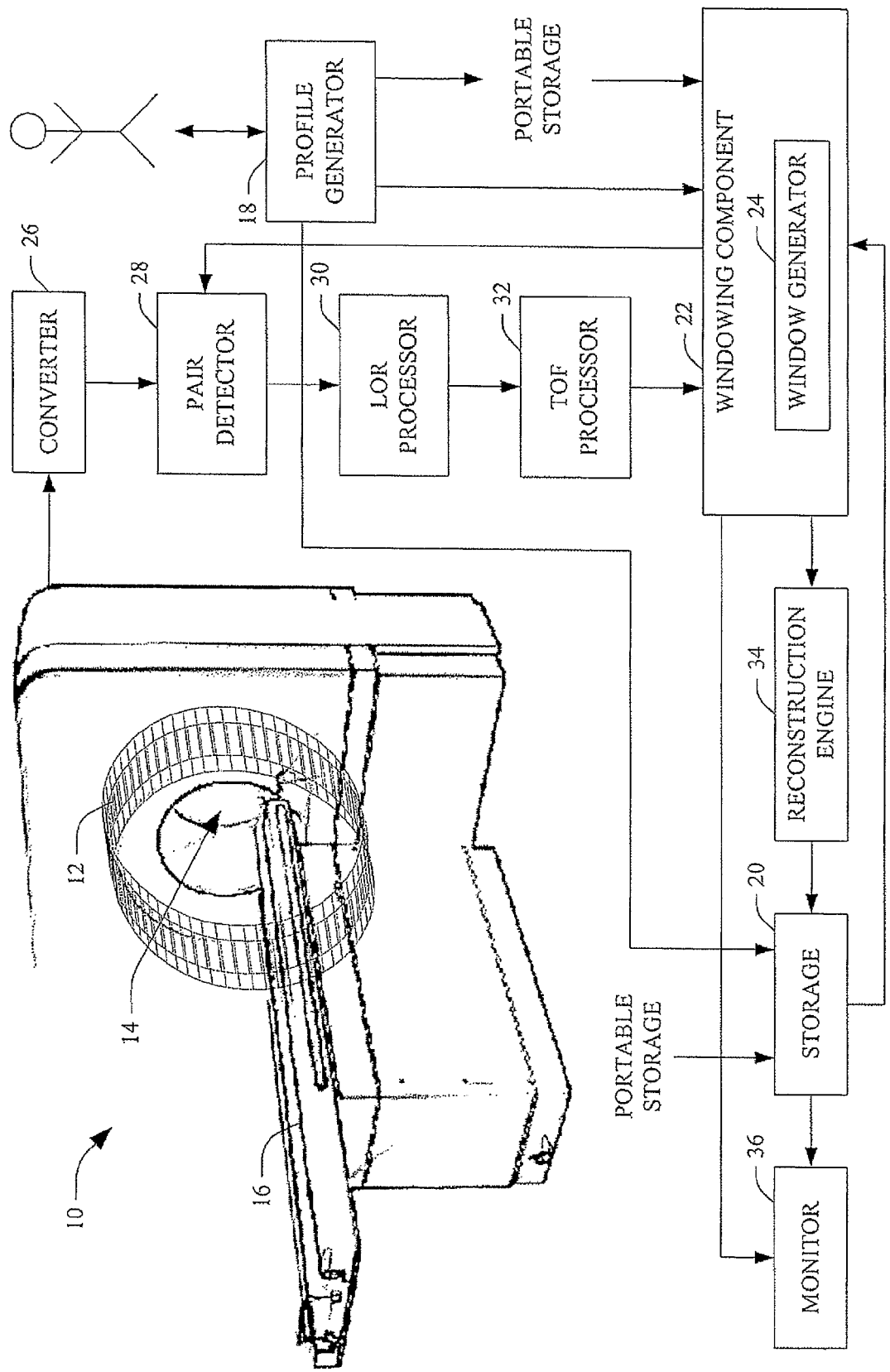
FIG. 1 illustrates an exemplary imaging system that uses a profile of a subject for dynamically adjusting an acceptance window.

FIG. 1 illustrates an exemplary imaging system 10, such as a time-of-flight Positron Emission Tomography (TOF-PET) scanner. In an illustrated embodiment, the imaging system 10 uses a profile of a subject to dynamically adjust a window that determines which detected radiation events are accepted for reconstruction and which detected radiation events are rejected. This facilitates identifying LORs attributable to scatter radiation, randoms, other false annihilations, and/or other extraneous data prior to reconstructing images.

The imaging system 10 includes the ring of radiation detectors 12 (e.g., hundreds, thousands, etc.) arranged around a scanner defined imaging region 14 to detect radiation events (e.g., gamma rays) emitted from within the scanner imaging region 14. As depicted, the plurality of radiation detectors 12 can be arranged in multiple rings (e.g., two, ten, a hundred, etc.) of detectors along an axial direction. A typical detector module is associated with one or more scintillation crystals, each of which produces a scintillation of light (a light photon) when struck by a radiation event such as a gamma ray (a gamma photon) produced from positron annihilation. The light photon produced by each crystal is received by one or more photodetectors (not shown) such as photomultiplier tubes, photodiodes, etc. The photodetectors convert the light photon into a representative electrical signal. Each detector may also be associated with processing circuitry (not shown) that provides signal amplification, filtering, conditioning, etc. The imaging system 10 further includes a support mechanism 16 for positioning a subject in the scanner imaging region 14.

Prior to scanning a subject with the imaging system 10, a profile of the subject is generated via a profile generator 18. The generated profile provides an outline, a map, a perimeter, a contour, etc. of the subject and defines a size, shapes, etc. of the volume of interest or subject. The profile generator 18 can be any device that generates profiles. For example, in one instance, the profile generator 18 can include another imaging modality such as a computed tomography (CT), x-ray, magnetic resonance (MR), etc., which is used to generate the profile. In another instance, the profile generator 18 can include a nuclear camera. For instance, the imaging system 10 or other device with a nuclear camera can be operated in a transmission mode to generate the profile. In yet another instance, the profile generator 18 can include and use laser technology (e.g., via laser gauging) to generate the profile. In yet another instance, the subject profile is manually selected from a menu of standard shapes and sizes.

The generated profile can be stored locally within the profile generator 18, on portable storage media (e.g., CD, DVD, optical disk, magnetic tape, hard disk, floppy disk, etc.), and/or transferred (e.g., via the Internet, a bus, a backplane, a cable such a USB, etc., the portable storage media, etc.) to the imaging system 10 and stored in a storage component 20, a windowing component 22, and/or in other data storage areas, including various types of volatile and/or non-volatile memory. Additional profiles of the subject can be generated by similar and/or different techniques, at similar and/or different moments in time (e.g., the same day, years apart, etc.). Profiles generated for one or more patients can be stored in a database, an electronic library, a look-up-table or the like. In instances where one or more profiles of the subject have been previously generated and stored, a suitable stored profile(s) can be selected, loaded and used. In some instances, two or more profiles for the subject can be averaged (e.g., via uniform or non-uniform weighting) to obtain the profile to be used. In another instance, for example, where the subject is not associated with a stored profile, one or more stored profiles associated with another subject can be selected, loaded and used for the subject.

In preparation for imaging the subject with the imaging system 10, a suitable radiopharmaceutical is administered to the subject and the subject is positioned within the imaging region 14. The radiopharmaceutical undergoes radioactive decay, which results in an emission of positrons. Each positron interacts with one or more nearby electrons and annihilates into two oppositely directed (180 degree) gamma rays having energies of about 511 keV each. The two oppositely directed gamma rays may strike opposing detectors at substantially the same time, or coincidentally, when positions originate equidistant from the pair of detectors. There may be a slight time offset between coincident events due to the different travel distances.

As described above, the detector 12 generates electrical signals which are conveyed to a converter 26, which digitizes and time stamps the signals. A pair detector 28 identifies pairs of substantially simultaneous or coincident gamma ray detections belonging to corresponding electron-positron annihilation events based on the time stamps. This processing can include energy windowing (e.g., discarding radiation detection events outside of a selected energy window disposed about 511 keV) and coincidence-detecting circuitry (e.g., discarding radiation detection event pairs temporally separated from each other by greater than a selected time-window). In one embodiment, the timing of this windowing is based on the bore-defined imaging region 14 and on the intrinsic timing resolution of the system. In another, it is based on a patient-defined imaging region, i.e., the profile generated by the profile generator 18, and the intrinsic time resolution of the system.

Upon identifying event pairs, a line of response (LOR) processor 30 processes the spatial information (e.g., detection locations) for each pair of events to identify a spatial LOR connecting the locations of two coincident gamma ray detections. Since the two gamma rays emitted by a positron-electron annihilation event are oppositely spatially directed, the electron-positron annihilation event is known to have occurred somewhere on the LOR. In TOF-PET, the radiation detectors 12 and the time stamping of the converter 26 have sufficiently high temporal resolution to detect a time-of-flight (TOF) difference between the two substantially simultaneous gamma ray detections. A TOF processor 32 analyzes the time difference between the times of each event of the coincident pair to localize the positron-electron annihilation event along a LOR that resides within the defined volume of the subject.

A window generator 24 generates a dynamic acceptance window for the subject based on the profile of the subject and an intrinsic resolution of the imaging system (which can also be stored within the storage component 20). That is, based on the profile, the location of the profile relative to the center of the bore, the time resolution of the system, and the detection location (location of the LOR), the window generator 24 geometrically calculates for each LOR that intersects the profile, the relative detection time window that localizes an event within the profile. The dynamic window applied by the windowing component 22 filters detected events prior to reconstruction based on the location of each positron-electron annihilation event along a line of response (LOR). This can be achieved by mapping the time stamp of the event to a corresponding location on the profile of the subject to obtain the window for that moment in time and location in space. Since the profile of the subject varies with the anatomy of the subject, the window varies depending on the anatomy being imaged. Any LOR that crosses the field-of-view (FOV), but fails to intersect the window, which defines a region of interest of the subject, is discarded. Thus, the window applied by the windowing component 22 is dynamically changed based on the location in space of each LOR. LORs which do not cross the profile have a zero window, i.e., are deleted.

Using the profile of the subject, the window can be defined to be a maximum extent of the actual subject, as determined by the profile, plus a tolerance or margin. The margin typically is set to a full width tenth max (FWTM) of the imaging system timing resolution. As an example, a time resolution of about 500 picoseconds (ps) (full width half max, or FWHM) results in a FWTM of about 900 ps (1.8*FWHM for a Gaussian) that corresponds to 27 cm (3.0e10 cm/s*900 ps). This results in a dynamic window that changes (e.g., widens and narrows) during imaging based on the profile of the portion (e.g., anatomy) of the subject through which the LOR passes so that only data from LORs in which the TOF measurement shows that the radiation event could have occurred within the subject are kept. By following the contour of the subject and rejecting events outside of the window, scatter, randoms, and other extraneous events can be discarded prior reconstruction.

By way of illustration, assume a brain protocol is associated with a field of view (FOV) of 20 cm (i.e., the patient profile is a 20 cm cylinder centered in the bore) and an imaging system with an 80 cm bore diameter. Using a conventional technique in which the size of the bore-defined window is set to about the bore size, the window would be set to about 80 cm (2.7 nanoseconds (ns)). The bore-defined timing window in one embodiment is applied by the pair detector 28. The windowing component 22 uses the profile of the subject to substantially reduce the size of the window, for example, to about 47 cm (1.57 ns), which is a substantial reduction relative to the 80 cm window. Using solid state silicon photo-multipliers (Si—PMs), which are expected to achieve an order of magnitude improvement in timing resolution relative to photo-multiplier tubes, and assuming a 50 ps FWHM and 90 ps FWTM (or 2.7 cm) imaging system resolution, the window size could be reduced further to about 22.7 cm (0.757 ns).

The window can be refined by additionally considering trigger channel bankpair angles. For example, in one instance, each trigger channel bankpair angle can be used to specify an angular window allowance as a function of the profile of the subject. By way of example, the filtering of the events can be done by applying an acceptance window based on how the LORs of the associated bankpair pass through the profile. With a centered cylinder, bankpairs that have LORs that pass through the center of the cylinder would have the largest acceptance window, while bankpairs with LORs that only pass through an edge of the subject, for example, can have a smaller acceptance window since the possible difference in the time of flight of each photon is more constrained. The resulting window hugs the subject profile to a greater extent relative to the other above described technique.

Additionally or alternatively, pre-defined windows that are based on imaging protocols can be stored in the storage component 20 and used during imaging subjects. For example, the imaging system 10 may have two or more default windows. For instance, there may be one or more predefined windows for head studies (e.g., infant, child, adult, etc., protocols) and one or more different predefined window for body studies (e.g., infant, child, adult, etc., protocols). In this example, the window(s) used for a particular study depends on the protocol selected by the clinician. The one or more predefined windows may also be based on particular anatomy and/or any user defined volume of interest. For instance, the system 10 can store and/or use one or more predefined windows corresponding to a brain, a liver, a kidney, a heart, etc. Such windows may be generated based on various characteristics of subjects like age, sex, weight, height, etc. such that there may be one or more predefined windows for each particular anatomy.

The windowing component 22 filters the localized events via a window, for example, the dynamic, the refined dynamic, or the protocol based coincidence timing windows described above in detail. The windowing component 22 can retrieve a suitable window from the storage component 20 or generate one in real-time via the window generator 24 based on the LOR location. As discussed previously, each positron-electron annihilation event is filtered based its location along a corresponding LOR in which events outside of the profile are discarded and events within the profile are used to reconstruct images.

With the dynamic and the refined dynamic windows, the windows dynamically change (e.g., widen and narrow) during imaging based on the profile of the portion (e.g., the anatomy) of the subject through which the LOP passes so that only data from LORs in which the TOF measurement shows that the radiation event could have occurred within the subject are accepted. Thus, during imaging, the window varies with the actual shape of the subject and follows the contour of the subject. Such discrimination facilitates discarding a substantial amount of scatter, randoms, and other extraneous events prior reconstruction.

With the protocol based windows, the windows also dynamically change depending on the anatomy being imaged. For instance, a head based window is used when imaging the head. However, when transitioning from the head to the shoulders, a relatively wider shoulder based window is used. Similarly, when transitioning from the torso to the lower extremities, another window that conforms more to such extremities is used. The protocol based windows typically provide coarser filtering resolution relative to the dynamic and refined dynamic windows, but greater filtering resolution relative to conventional single window systems.

It is to be appreciated that the subject need not be centered in the field-of-view for any of the above examples. That is, the subject can be off-center. By using an asymmetric time stamp or window, the region of interest can be shifted off center, for example, to the left or right of center in order to compensate for the positioning of the subject.

The events that are passed through the windowing component 22 include a large number of positron-electron annihilation events that form a set of histoprojections that are conveyed to the reconstruction engine 34, which reconstructs the histoprojections to generate one or more images using a suitable reconstruction algorithm such as filtered backprojection, iterative backprojection with correction, etc. Since this data has already been processed by the windowing component 22 to discard a substantial portion of extraneous data (e.g., randoms, scatter, etc.) that does not contribute to image reconstruction, the filtering load on the reconstruction engine 34 is reduced and its processing capabilities can be leveraged to increase performance, for example, to increase the relative rate of reconstructing images. Thus, reconstruction is not slowed by processing (e.g., sorting through) numerous data values which are removed prior to rendering images or compensated for in the reconstructed image. In addition, image quality is improved since randoms, scatter, etc. reduce contrast.

The raw data and/or reconstructed images can be stored (e.g., in the storage component 20), printed, archived, filmed, processed, transferred to another device, displayed on a monitor 36, etc. A radiologist or other suitable clinician can use the raw data and/or reconstructed image to control the imaging system 10, diagnose the subject, etc.

Figure 2:
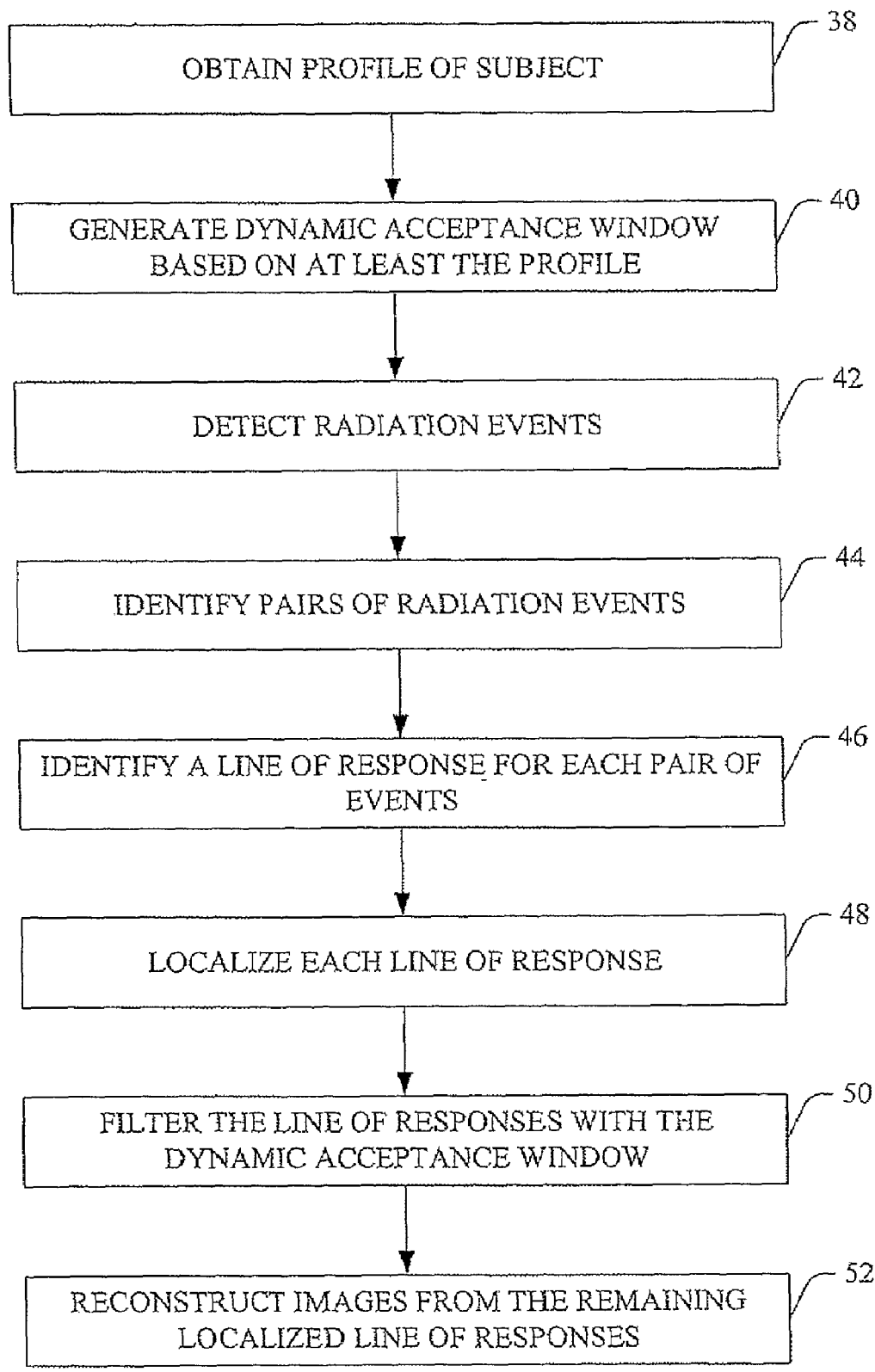
FIG. 2 illustrates a method that uses a profile of a subject to dynamically adjust an acceptance window for an imaging system.

FIG. 2 illustrates a method that uses a profile of a subject to dynamically adjust an event acceptance window for the imaging system 10. At reference numeral 38, a profile of a subject that will be scanned by the imaging system 10 is obtained. As described above, the profile can be acquired through any known means (e.g., CT, MR, PET, laser, etc.) of generating an outline, a map, a perimeter, a contour, etc. of the subject. The generated profile can be stored locally within the profile generator 18, on portable storage media, and/or transferred to the imaging system 10 and stored therein in the storage component 20.

At 40, the profile along with the resolution of the imaging system 10 is used to to generate a dynamic event acceptance window for the subject. In one embodiment, the LORs which intersect the profile are determined, and for each profile-intersecting LOR, a symmetric or asymmetric window, which identifies temporal localization along the ray that at least partially falls in the profile, is determined. The window can be saved in various formats such as a LUT, a polynomial, an equation, etc. When the LOR coordinates are input into a LUT, the window for the input LOR is retrieved. Alternatively, the window can be calculated in real-time from the profile and the resolution of the imaging system 10 for each pair.

At 42, radiation events associated with a subject are detected and processed by the imaging system 10. A radiopharmaceutical which was administered to the subject undergoes radioactive decay, which results in an emission of positrons that interacts with one or more nearby electrons and annihilate into two oppositely directed gamma rays. The gamma ray may strike opposing detectors at substantially the same time, or coincidentally, producing a light photon, which is converted to a representative electrical signal and processed (e.g., amplified, filtered, conditioned, etc.). The electrical signals are conveyed to a converter 26, which digitizes and time stamps the signals.

At 44, the pair detector 28 identifies pairs of substantially simultaneous gamma ray detections belonging to corresponding electron-positron annihilation events based on the time stamps. This processing can include energy windowing and coincidence-detecting circuitry as well as other processing. At 46, the line of response (LOR) processor 30 processes the spatial information for each pair of events to identify a spatial LOR connecting two coincident gamma ray detections, which are known to have occurred somewhere on the LOR. Optionally, data for LORs that do not intersect the profile can be deleted at this point. At 48, a TOF processor 32 analyzes the time difference between the times of each event of the coincident pair to localize the positron-electron annihilation event along a LOR.

At 50, the windowing component 22 filters the localized event pairs through the dynamic event acceptance window to apply the window corresponding to the LOR. In the pre-calculated LUT embodiment, the LOR coordinates or detection pair locations are input into the LUT to retrieve the window which is applied to the event pair. Alternatively, steps 48 and 50 are reversed to save the processing time to localize events that are later discarded. LORs that do not intersect the profile are removed by selection of a non-achievable coincidence window. In another embodiment, the window can be configured to follow a maximum extent of the subject plus a margin (e.g., FWTM). This can be achieved by mapping the time stamps of each event to a corresponding location on the profile of the subject to obtain the window for that event, which is typically different from windows for other events. The localized LORs whose events fail to fall in the window are discarded.

At 52, a reconstruction engine 34 reconstructs images from the localized LORs that pass through the profile. By using the dynamic window described herein, a substantial portion of extraneous data (e.g., randoms, scatter, etc.) that does not contribute to image reconstruction is discarded prior to reconstruction. Thus, reconstruction is not slowed by processing (e.g., sorting through) numerous data values which are filtered during image rendering or compensated for in the reconstructed image, which improves reconstruction performance (e.g., the rate at which images are reconstructed) and improves image quality since such extraneous data reduces contrast.

The raw data and/or reconstructed images can be stored, printed, archived, filmed, processed, transferred to another device, displayed, etc., and a suitable clinician can use this data to control the imaging system 10, diagnose the subject, etc.

Figure 3:
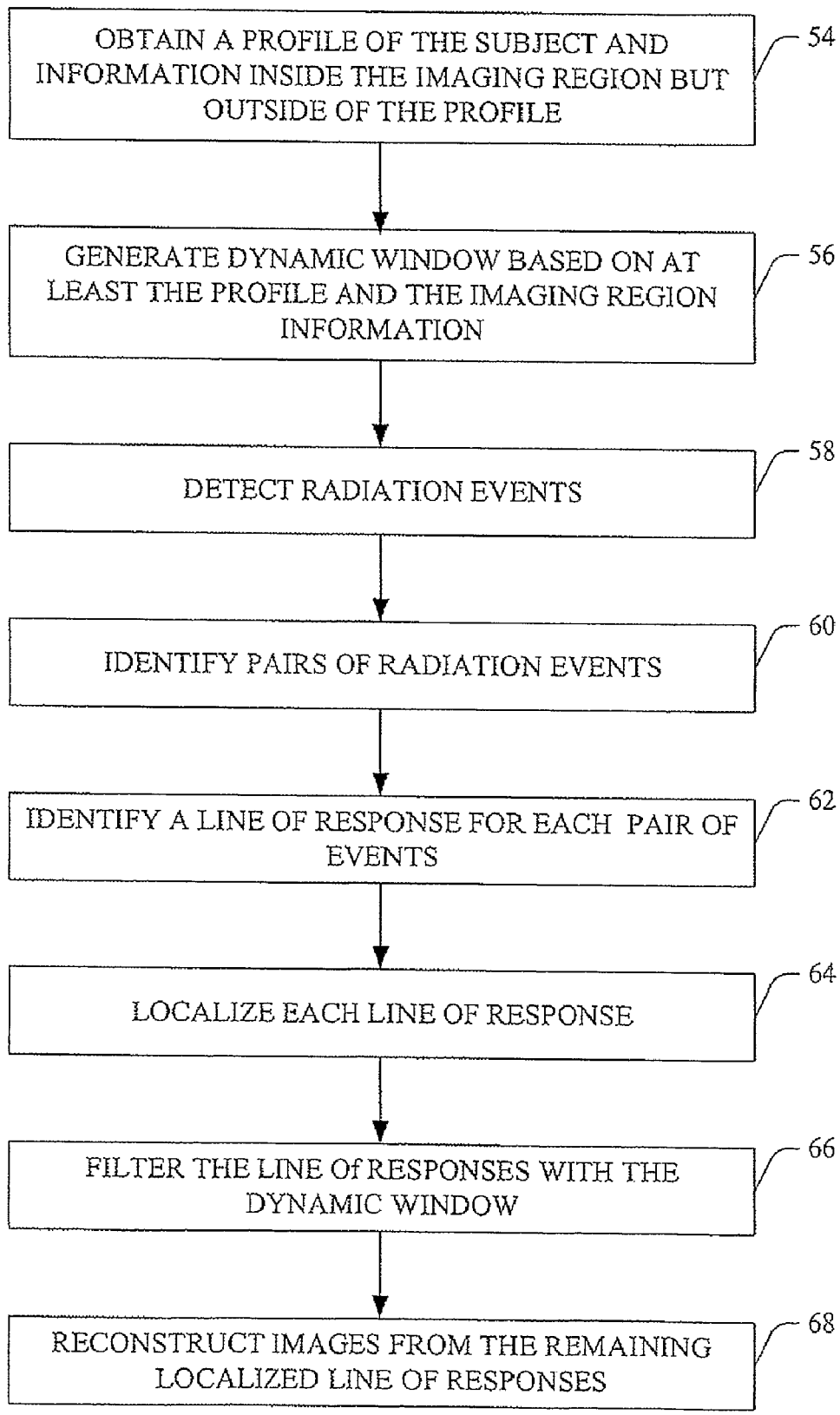
FIG. 3 illustrates a method that uses a profile of a subject and information regarding the imaging region outside of the profile to dynamically adjust an acceptance window for an imaging system.

FIG. 3 illustrates an alternative method that uses a profile of a subject and information about regions of the imaging region 14 are outside of the profile to dynamically adjust an acceptance window for the imaging system 10. At 54, a profile of a subject and an angular allowance are obtained. The profile and the angular allowance can be obtained as described above or through variations thereof. At 56, the profile, the angular allowance, and the resolution of the imaging system 10 are used to generate a dynamic window for the subject. The resulting window follows or hugs the subject to a greater extent relative to the technique that does not consider the regions of the imaging region 14 outside of the profile.

At 58, radiation events are detected and processed (e.g., converted to electrical signals, conditioned, amplified, digitized, time stamped, etc.) by the imaging system 10. At 60, the pair detector 28 identifies pairs of substantially simultaneous or coincident gamma ray detections belonging to corresponding electron-positron annihilation events based on the time stamps. At 62, the line of response (LOR) processor 30 processes the spatial information for each pair of events to identify a spatial LOR connecting two coincident gamma ray detections, which are known to have occurred somewhere on the LOR. At 64, a TOF processor 32 analyzes the time difference between the times of each event of the coincident pair to localize the positron-electron annihilation event along a LOR.

At 66, the windowing component 22 determines whether the localized portion of each LOR falls within or outside of the profile. For example, the corresponding window determined in step 56 for the LOR is applied to the detection times of the event pair that defined the LOR to see if it is valid data, i.e., represents an event that could have occurred within the profile. The valid localized LORs are conveyed to the reconstruction engine 34 which reconstructs images from the localized LOR to generate an image of the region of interest in the profile. The raw data and/or reconstructed images can be stored, printed, archived, filmed, processed, transferred to another device, displayed, etc., and a suitable clinician can use this data to control the imaging system 10, diagnose the subject, etc.

Figure 4:
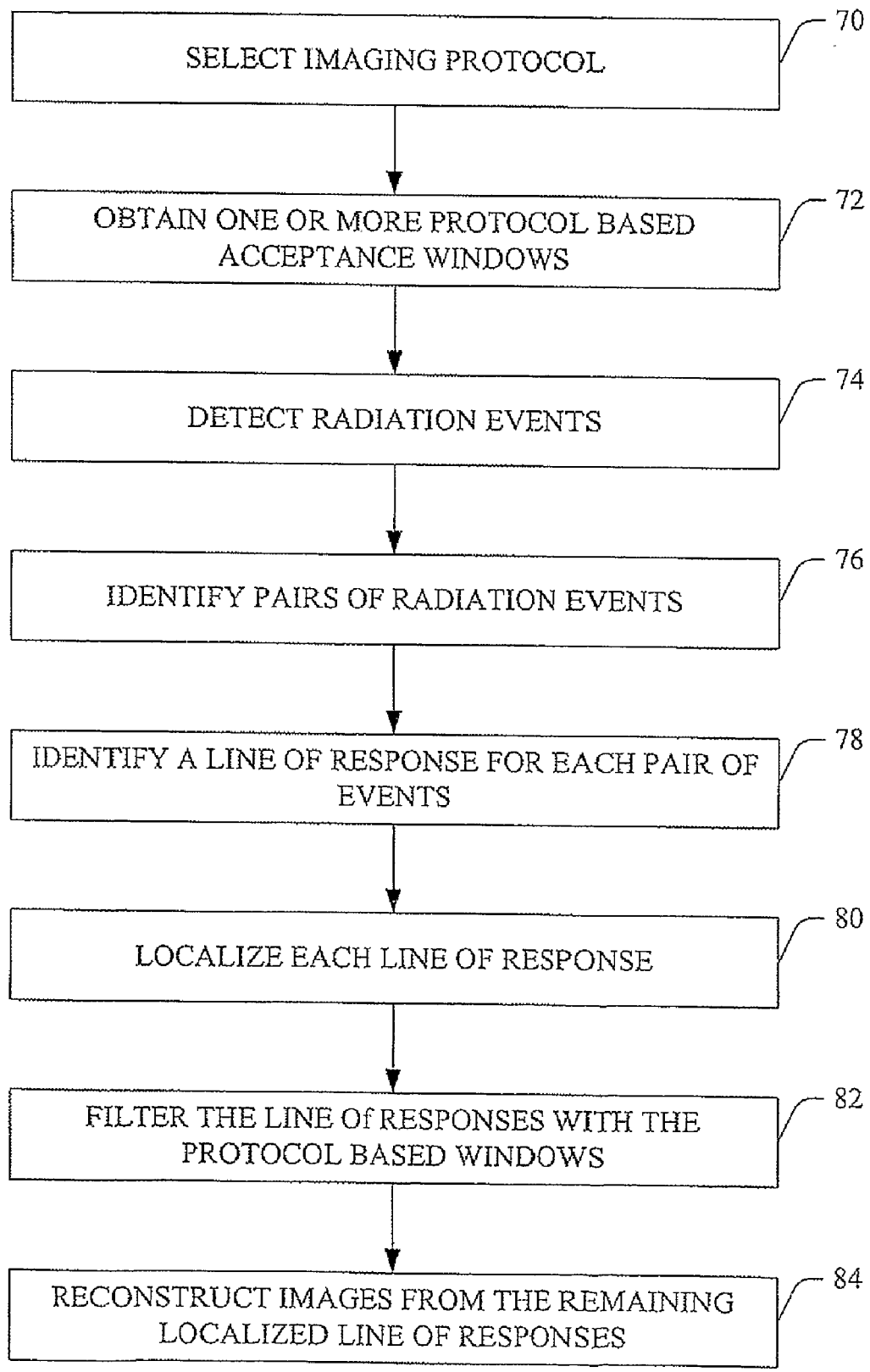
FIG. 4 illustrates a method that uses default acceptance windows that are based on a selected imaging protocol.

FIG. 4 illustrates another alternative method that dynamically adjusts an acceptance window for the imaging system 10. This method uses a window that is based on an imaging protocol selected by the clinician. At 70, the clinician selects one or more imaging protocols. For example, the head can be profiled as a cylinder and the torso as an ellipse. The diameter of the cylinder and the major and minor axes of the ellipse are preselected based on child, adult, obese adult, etc. At 72, the pre-calculated dynamic windows based on the selected imaging protocol(s) are retrieved from the storage component 20. At 74, radiation events are detected and processed by the imaging system 10. At 76, the pair detector 28 identifies pairs of substantially simultaneous or coincident gamma ray detections belonging to corresponding electron-positron annihilation events based on the time stamps. In one embodiment, the pairs are determined from the bore diameter determined coincidence times. In another embodiment, the coincident times are reduced based on the major axis of the ellipse for a head only protocol, the diameter of the cylinder.

At 78, the line of response (LOR) processor 30 processes the spatial information for each pair of events to identify a spatial LOR connecting two coincident gamma ray detections, which are known to have occurred somewhere on the LOR. At 80, the TOF processor 32 analyzes the time difference between the times of each event of the coincident pair to localize the positron-electron annihilation event along the identified LOR. At 82, the windowing component 22 filters the localized LORs with the protocol based coincidence timing windows. In a special example in which the head only is imaged and modeled as a cylinder centered on the axis of the bore, if the pair identification step 78 detects coincidence with a window based on the cylinder diameter, coincidence steps 78 and 82 become redundant allowing step 82 to be eliminated. At 84, a reconstruction engine 34 reconstructs images from the accepted events. The raw data and/or reconstructed images can be stored, printed, archived, filmed, processed, transferred to another device, displayed, etc., and a suitable clinician can use this data to control the imaging system 10, diagnose the subject, etc.

With respect to the method described in FIG. 2-4, it is to be understood that the subject need not be centered in the field-of-view for any of the above examples. That is, the subject can be off-center. By using an asymmetric coincidence timing filter, the subject-defined region can be shifted off center, for example, to the left or right of center in order to compensate for the positioning of the subject.

In addition, even though these methods are described through a series of acts, it is to be understood that in various instances, the illustrated acts can occur in a different order. In addition, in some instance, the one or more of the acts can concurrently occur with one or more other acts. Moreover, in some instance more or less acts can be employed.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method of reconstructing time-of-flight images, comprising:
obtaining a profile of a subject to be imaged in an examination region of an imaging system, the profile includes a volume of interest within the subject;
generating a dynamic radiation event acceptance window based at least on the profile;
detecting events associated with radiation emitted from the subject and generating corresponding electronic data;
filtering the electronic data with the dynamic radiation event acceptance window in which electronic data attributable to radiation events located outside the profile are discarded; and
reconstructing images from the remaining electronic data.

2. The method as set forth in claim 1, further including:
identifying pairs of substantially simultaneous events;
determining a spatial line of response (LOR) connecting each identified event pair; and
filtering the event pairs associated with each LOR with the dynamic acceptance window, which dynamically changes shape to follow the profile of the subject, wherein event pairs that fall within the acceptance window are retained and event pairs that fall outside of the acceptance window are discarded, the LORs corresponding to the retained event pairs being reconstructed.

3. The method as set forth in claim 2, further including:
locating a position of each event along its corresponding LOR.

4. The method as set forth in claim 2, further including:
determining a suitable acceptance window for each event pair by mapping a corresponding time stamp of each event of the pair to the profile and using the acceptance window for that portion of the profile to filter the event pair.

5. The method as set forth in claim 2, further including discarding LORs that do not intersect the profile.

6. The method as set forth in claim 1, further including:
generating the acceptance window based on the profile of the subject and an intrinsic resolution of the imaging system.

7. The method as set forth in claim 1, further including:
generating the acceptance window based on the profile of the subject, information about the imaging region outside of the profile, and an intrinsic resolution of the imaging system.

8. The method as set forth in claim 1, further including:
defining the acceptance window to be a maximum extent of the subject, as determined by the profile, plus a margin.

9. The method as set forth in claim 1, further including:
storing the acceptance window in a storage component of the imaging system as a look-up-table or a discrete set of data that is used to generate the window.

10. The method as set forth in claim 1, further including:
generating the acceptance window one of: prior to imaging the subject and in real-time while imaging the subject.

11. The method as set forth in claim 1, further including:
obtaining the profile through one of a computed tomography, nuclear magnetic resonance, nuclear imaging, and laser technology.

12. The method as set forth in claim 1, wherein the subject is off-center relative to the examination region and further including:
using an asymmetric timing window to compensate for the off-center positioning when removing electronic data attributable to radiation events occurring outside the profile.

13. The method as set forth in claim 1, wherein removing electronic data attributable to radiation events locating outside the profile includes:
from relative detection times of the detected radiation events, determining pairs of detected radiation events that correspond to radiation emitted from within the profile.

14. The method as set forth in claim 1, wherein obtaining the profile includes:
selecting and sizing one or more geometric volumes based on a selected imaging protocol.

15. A time-of-flight positron emission tomography (TOF-PET) imaging system programmed implement the method of claim 1.

16. A time-of-flight imaging apparatus, comprising:
a window generator that generates a dynamic acceptance window based on a profile of a subject and an intrinsic resolution of the imaging systems;
a plurality of radiation detectors that generate signals indicative of each radiation event detection;
a line of response (LOR) processor that identifies a spatial LOR connecting a pair of radiation detections corresponding to a common radiation event;
a windowing component that filters the radiation event detections through a dynamic window; and
a reconstruction engine that reconstructs images based on the remaining non-filtered radiation event detections.

17. The apparatus as set forth in claim 16, wherein the windowing component rejects LORs that do not intersect the profile.

18. The apparatus as set forth in claim 16, further including:
a time-of-flight (TOF) processor that analyzes relative detection times of the pair of radiation detections that corresponds to each LOR to localize the radiation event along the LOR.

19. The apparatus as set forth in claim 18, wherein the windowing component rejects LORs that intersect the profile and whose localized radiation event falls outside the profile.

20. The apparatus as set forth in claim 16, further including:
a window generator that generates the window based on the profile of the subject, an angular coincidence window allowance, and an intrinsic resolution of the apparatus.

21. The apparatus as set forth in claim 16, wherein the dynamic window includes two or more protocol based windows.

22. The apparatus as set forth in claim 16, wherein the dynamic window corresponds to a user defined volume of interest within the subject.

23. The apparatus as set forth in claim 16, wherein the windowing component filters each LOR based on a shape of the dynamic acceptance window, which dynamically changes to follow the profile of the subject.

24. A time-of-flight imaging system, comprising:

a window generator that generates a coincident window look-up-table based at least on a profile of a subject;

a plurality of radiation detectors that generate signals indicative of each detected radiation event;

a line of response (LOR) processor that identifies a spatial LOR connecting each pair of coincident radiation events;

a windowing component that filters the pairs of coincident radiation events by mapping a time stamp of each event to the coincident window look-up-table to obtain an acceptance window in which radiation events located outside of the acceptance window are discarded; and a reconstruction engine that reconstructs images based on the retained pairs of coincident radiation events.

* * * * *